United States Patent [19]

Ridoux

[11] Patent Number: 4,983,583
[45] Date of Patent: Jan. 8, 1991

[54] GRANULATED COMPOSITIONS OF POLYSACCHARIDES, PROCESS FOR THEIR PREPARATION AND USE

[75] Inventor: Claude Ridoux, Isle-sur-Sorgue, France

[73] Assignee: Sanofi, Societe Anonyme, Paris, France

[21] Appl. No.: 260,750

[22] Filed: Oct. 21, 1988

[30] Foreign Application Priority Data

Oct. 21, 1987 [FR] France ................ 87 14559

[51] Int. Cl.$^5$ .............. A61K 9/34; A61K 9/36; C07H 1/00
[52] U.S. Cl. ................................ 514/54; 514/53; 536/114; 536/1.1; 536/2.0; 536/112; 536/102; 252/8.513; 424/439; 424/499
[58] Field of Search .............. 514/54, 53; 536/114, 536/112, 1.1, 2.0, 102; 426/576, 613; 424/479, 480, 481, 439, 499; 252/8.513

[56] References Cited

U.S. PATENT DOCUMENTS

| | | | |
|---|---|---|---|
| 4,517,216 | 5/1985 | Shim | 426/573 |
| 4,729,897 | 3/1988 | Poppe | 426/96 |
| 4,792,452 | 2/1988 | Howard et al. | 514/54 |

OTHER PUBLICATIONS

McMullen et al., Journal of Pharmaceutical Sciences, vol. 17, No. 6 Jun. 1982, pp. 628–632.

*Primary Examiner*—Ronald W. Griffin
*Assistant Examiner*—Pamela S. Webber
*Attorney, Agent, or Firm*—Foley & Lardner, Schwartz, Jeffery, Schwaab, Mack, Blumenthal & Evans

[57] ABSTRACT

The present invention relates to granulated compositions of thickening and viscosity-raising polysaccharides having few anionic groups, wherein the polysaccharide particles are coated with hydrolyzed gelatin.

9 Claims, No Drawings

GRANULATED COMPOSITIONS OF POLYSACCHARIDES, PROCESS FOR THEIR PREPARATION AND USE

The present invention relates to compositions of thickening polysaccharides, with high dispersibility in water, consisting of particles of polysaccharides coated with a hydrolysed gelatin.

It is known that polysaccharides which are used as thickening and viscosity-raising agents for aqueous media are difficult to disperse in water: they aggregate and form lumps. In order to dissolve a powder of these polysaccharides in water it is thus necessary to introduce them into the medium little by little with vigorous stirring or after having wetted the powder beforehand, other means have also been suggested to facilitate the dissolution of such powders, such as:

treatment of the polysaccharide with aldehydes, for example with formaldehyde or glyoxal, a treatment which improves their dispersibility but decreases the rate of dissolution of the polymers.

addition to the polysaccharide or to the medium to be made viscous of solubilizing additives such as sodium lignosulfonate added to xanthan and scleroglucan according to the patent FR-A-2577982, or such as the sugars added in very high proportions (8 to 10 fold) to pectins.

dehydration in a fluidized bed of a solution of the polysaccharide placed on an inert divided support from which the anhydrous polysaccharide is easily removed, according to EP A-206368, prior wetting with an alcohol or a polyol, especially of the pectins.

It has now been found that compositions of thickening and viscosity-raising polysaccharides, wettable and easy to disperse in an aqueous media, can be obtained by coating the particles of polysaccharide with hydrolysed gelatin, provided that said polysaccharides do not have many anionic groups.

The improvement of the wettability and dispersibility of gelatin by coating with hydrolysed gelatin has been described in FR A-2586030, but it cannot be concluded from this that the same solution may be applied to certain polymers of very different nature and properties.

According to the invention, the polysaccharide powder is treated by a standard process in a granulator with an aqueous solution of a suitably chosen gelatin. This gives rise to a composition of larger granulometry than that of the starting material, and another advantage of the invention is the removal of the fines of the polysaccharide powder with, in particular, an improvement in the flowability of the product.

The granulates, object of the invention, may be prepared with thickening and viscosity-raising polysaccharides resulting from either an extraction from plant material such as the galactomannans, starches and the natural pectins or their amidated derivatives, or from the fermentation of glucose by micro-organisms, such as xanthan, dextran and scleroglucan or from a mixture thereof. The improvement in the wettability and dispersibility is particularly perceptible in the case of xanthan and galactomannans: the guar and the locust-bean, and it is very clean-cut even for sparingly methylated pectins; on the other hand, it is practically zero for polysaccharides having many anionic groups, whether in the form of salts or not, such as the alginates and carrageenan, and these latter do not form part of the invention.

The hydrolysed gelatin used for the granulation is a gelatin of molecular weight from 1000 to 50,000 daltons and preferably from 3000 to 15,000 daltons, resulting from the hydrolysis by enzymatic or chemical means of a gelatin obtained in a standard manner by hydrolysis of the collagen of the skins and bones of animals; this hydrolysed gelatin is soluble in water at 20° C., no longer possesses a measurable gel strength and its 20% (wt/v) aqueous solutions have a viscosity varying between 1.5 mPa.s and 75 mPa.s, as measured at 25° C. by the method using a viscosimetric delivery pipette; this method of measurement is described in the book "Standard methods for the sampling and testing of gelatins" edited by Gelatin Manufacturers Institute of America Inc.. These grades of hydrolysed gelatin are commercially available or can be prepared by using the procedures described particularly in "Novo enzyme Information 1636-GB" starting from a gelatin of type A or B resulting from the hydrolysis of the collagen of porcine and bovine skins and bones.

The granulates, object of the invention, usually contain from 0.5 to 5.0% by weight of hydrolysed gelatin with respect to the weight of the polysaccharide.

The granulation can be carried out in a standard granulator by potting followed by granulation, in a gas-operated fluidized bed granulator or in a rapid-action granulator, into which the powdered polysaccharide is introduced with a solution of hydrolysed gelatin, either an aqueous solution or an hydroalcoholic solution of gelatin. The conditions of granulation depend on the physical chemical properties of the polysaccharide and of the hydrolysed gelatin; the air flow in the air-operated fluidized bed obviously depends on the size and density of the particles.

In the case of a galactomannan in an air-operated fluidized bed granulator, an aqueous solution containing from 2 to 25% by weight and preferably 5 to 10% of hydrolysed gelatin is sprayed on to the polysaccharide powder in suspension in the fluidized bed, the air being introduced at a temperature varying between 20° C. and 80° C. and preferably between 40° C. and 70° C.

The granulated compositions of polysaccharides according to the invention can be used in all of the standard applications of polysaccharides in powder form; they are particularly advantageous for the preparation of products requiring aqueous rapid dilution, called instant products, in the fields of foodstuffs and pharmaceuticals and another object of the invention is the use of these granulates for the preparation of compositions to be diluted easily and rapidly to give stable aqueous suspensions for dietary or pharmaceutical purposes. Some of those granulated polysaccharides and especially the galactomannans even give rise to gels which form almost instantaneously, on dispersion and immediate swelling in an aqueous phase, at a concentration equal to or higher than 5%.

Among the applications to foodstuffs, mention may be made of the instant preparations for instant creams, custards and chocolate drinks.

In the pharmaceutical field, the introduction of granulates of polysaccharides into a powdered mixture of active principle and excipients makes it possible, when the active principle is insoluble in water, to obtain a formulation which gives a stable homogeneous suspension of the active principle, almost without need of stirring; they will find their application especially in the preparation of drinkable suspensions or creams, for example in pediatrics.

Granulates according to the invention can also be used advantageously for technical applications, for example in suspensions for sizing or in textile finishings.

Examples of the implementation of the invention are described below.

By definition, the dispersibility is measured by the time taken by the powder to be distributed throughout the whole of the liquid after having been deposited on the surface of the water; in order to determine this value, 1 or 2 g of the product to be studied are placed in a funnel, the closed stem of which is placed just above the surface of 100 ml of water which have been introduced into a 250 ml beaker and the time taken by the powder to penetrate into the liquid and be dispersed therethrough is measured either without stirring or with mechanical stirring (750 rpm) after opening of the stem of the funnel.

EXAMPLE 1

In a granulator of the Uniglatt type, marketed by the company Glatt-France, 400 g of guar powder are fluidized in an air bed at 65° C. and 200 ml of a solution at a temperature of about 20° C. and which contains 10% (wt/v) of hydrolysed gelatin is sprayed into this bed at a rate of 10 ml/min and at a pressure of $5 \times 10^4$ Pa.

The granulates are maintained in the fluidized bed for 5 min after the completion of spraying in order to dry them.

The hydrolysed gelatin used is an atomised gelatin, water-soluble at 20° C., with a molecular weight of 6000 daltons, obtained by enzymatic hydrolysis of a type B gelatin.

From a guar gum, such as that marketed by the company Mero Rousselot Satia (France) under the reference Viscogum ® HV 3000 A, possessing the following properties:

| | |
|---|---|
| apparent density | 0.727 g/ml |
| apparent volume | 1.375 ml/g |
| dispersibility of 2 g without stirring | |
| at 20° C. | 8 hours |
| at 60° C. | 3 hours 36 min |
| granulometry | 87% pass through a 200 mesh sieve | granulates containing 5% gelatin are obtained and are characterized by the following values:

| | |
|---|---|
| apparent density | 0.251 g/ml |
| apparent volume | 3.975 ml/g |
| dispersibility of 2 g without stirring | |
| at 20° C. | 9 seconds |
| at 60° C. | 3 seconds |
| granulometry | 31.45% pass through a 200 mesh sieve |

EXAMPLE 2

By applying the method indicated in Example 1, 400 g of xanthan powder are granulated with 400 ml of a 5% solution of the same hydrolysed gelatin which is introduced into the granulator at a pressure of $10^5$ Pa and a rate of 100 ml/min.

During granulation, the air is introduced at 65° C. and on completion of spraying the granulates are dried for 10 min with air at 60° C. The properties of the starting xanthan powder and the prepared granulates are presented in the following Table I:

TABLE I

| PROPERTIES | POWDER | GRANULATES |
|---|---|---|
| apparent density g/ml | 0.689 | 0.262 |
| apparent volume ml/g | 1.45 | 3.815 |
| dispersibility of 2 g, at 20° C. without stirring | 1 h 25 | 27 min |
| dilution in water with stirring at 20° C. | non-wettable lumps | no lumps |

EXAMPLE 3

A homogeneous mixture of 200 g of the xanthan powder used in the previous Example is granulated with 200 g of locust-bean powder by spraying 200 ml of a 6% solution of the hydrolysed gelatin used in Example 1, at a pressure of $7 \times 10^4$ Pa and a rate of 15 ml/min; the air is introduced into the granulator at 80° C.; on completion of granulation, drying is performed for 10 min.

The granulates contain 3% by weight of gelatin with respect to the weight of polysaccharide.

In another test, 350 ml of the same solution of hydrolysed gelatin are introduced to produce granulates containing 5% of the latter, instead of 3%.

In Table II are presented the properties of the mixture of starting powders and those of the granulates obtained; the 5% granulates really is instantly water dispersible.

TABLE II

| PROPERTIES | POWDER | 3% GRANULATES | 5% GRANULATES |
|---|---|---|---|
| apparent density g/ml | 0.735 | 0.575 | 0.273 |
| apparent volume ml/g | 1.36 | 2.74 | 3.66 |
| dispersibility of 2 g, at 20° C. without stirring | 15 mn with large lumps | 3 mn 30 with some lumps | 10 sec. homogeneous |
| dispersibility of 1 g at 20° C. with stirring | 5 sec. with large lumps | 5 sec homogeneous | 5 sec. homogeneous |

EXAMPLES 4 and 5

300 g of a highly methylated (HM) pectin powder or of a pectin sparingly methylated (LM) but amidated, such as that marketed under the reference Unipectine 325 NH 95 by Sanofi Bio Industrie (FR) are introduced into an air-operated fluidized bed at 45° C., and into it are sprayed 180 ml of a 5% aqueous alcoholic solution ($H_2O/C_2H_5OH$: 50/50: v/v) of hydrolysed gelatin (wt/v) at a rate of 10 ml/min and at a pressure of $5 \times 10^4$ Pa.

The granulates are maintained in the fluidized bed for 10 minutes after completion of spraying.

The properties of the starting powders and the granulates of the invention are presented in Table III.

TABLE III

| PROPERTIES | STARTING POWDER | | GRANULATES | |
| --- | --- | --- | --- | --- |
| | HM pectin | amidated LM pectin | HM pectin | amidated LM pectin |
| apparent density g/ml | 0.671 | 0.727 | 0.234 | 0.395 |
| apparent vol. ml/g | 1.49 | 1.375 | 4.28 | 2.53 |
| dispersibility of 2 g* | | | | |
| at 20° C. | non-wettable lumps | lentils at surface | 11 sec. (gel within 1 h) | immediate (gel within 45 min) |
| at 60° C. | non-wettable lumps | large lumps | 3 sec. (gel within 10 min) | immediate (gel within few minutes) |

*with manual stirring in the case of the starting powder, without stirring in the case of the granulates.

EXAMPLE 6

A LM non-amidated pectin is granulated with an aqueous solution of hydrolysed gelatin as described in Example 4 to produce 3% gelatin (wt/wt) granulates.

The results are presented in FIGURE IV.

TABLE IV

| PROPERTIES | Starting powder | Granulates |
| --- | --- | --- |
| apparent density g/ml | 0.690 | 0.292 |
| apparent volume (ml/g) | 1.45 | 3.43 |
| dispersibility of 2 g*: | | |
| at 20° C. | lumps | 9 sec. (gel within 45 min) |
| at 60° C. | non-wettable mass | 3 sec. (gel within 10 min) |

*without stirring in the case of the granulates; with manual stirring in the case of the powder.

I claim:

1. A powdered composition for dispersion in an aqueous solution to raise the viscosity of said solution, comprising granulated polysaccharide particles coated with hydrolysed gelatin, wherein said polysaccharide is selected from the group consisting of galactomannan, starch, natural or amidated pectin, xanthan, dextran, scleroglucan and mixtures thereof.

2. The composition according to claim 1 wherein said hydrolysed gelatin has a molecular weight from about 1000 to 50,000 daltons.

3. The composition according to claim 1, wherein said hydrolysed gelatin comprises 0.5 to 5.0% by weight, relative to the weight of said polysaccharide.

4. The composition according to claim 1, wherein said polysaccharide comprises a xanthan.

5. The composition according to claim 1, wherein said polysaccharide comprises a galactomannan.

6. The composition according to claim 1, wherein said polysaccharide comprises a natural or amidated pectin.

7. The composition according to claim 1, wherein said polysaccharide comprises a scleroglucan.

8. The composition according to claim 1, wherein said polysaccharide particles comprise a mixture of said polysaccharides.

9. Pharmaceutical, foodstuffs or industrial instant compositions having a viscosity-raising granulated composition component, wherein the improvement comprises a granulated composition according to claim 1.

* * * * *